great Britain

United States Patent [19]

Cheetham et al.

[11] Patent Number: 5,635,190
[45] Date of Patent: Jun. 3, 1997

[54] SOLUBILIZING AGENTS

[75] Inventors: Peter S. J. Cheetham; Thalie P. de Graaf, both of Bedford; Angela Janousek, Canterbury, all of Great Britain; Erich Klein, Graz, Austria; Stephen D. Watkins, Kent, Great Britain

[73] Assignee: Quest International B.V., Naarden, Netherlands

[21] Appl. No.: 433,499

[22] PCT Filed: Oct. 19, 1993

[86] PCT No.: PCT/EP93/02883

§ 371 Date: Sep. 19, 1995

§ 102(e) Date: Sep. 19, 1995

[87] PCT Pub. No.: WO94/10970

PCT Pub. Date: May 26, 1994

[30] Foreign Application Priority Data

Nov. 9, 1992 [EP] European Pat. Off. ............. 92310222

[51] Int. Cl.$^6$ ........................................................ A61K 7/48
[52] U.S. Cl. ..................... 424/401; 424/70.1; 514/547; 514/938; 510/159
[58] Field of Search ................. 424/401, 70.1; 252/170, 174.11, 174.19; 514/547, 938

[56] References Cited

U.S. PATENT DOCUMENTS 5,049,699  9/1991  Kotick ..................................... 560/180

Primary Examiner—Margaret W. Glass
Attorney, Agent, or Firm—Cushman Darby & Cushman IP Group Pillsbury Madison & Sutro LLP

[57] ABSTRACT

The invention related to the use of monoalkyl citrates having an alkyl group of 7–10 carbon atoms as solubilizing agents in perfumery, cosmetics, personal care and household products consisting of oil-in-water emulsions as well as to hydrophobic cosmetic, personal care and household product ingredients containing such monoalkyl citrates. The emulsions preferably contain at least 0.01% w/w of monoalkyl citrate. Especially prefereed in monooctyl citrate.

9 Claims, No Drawings

SOLUBILIZING AGENTS

The invention relates to the use of monoalkyl citrates as solubilizing agents in perfumery, cosmetics, personal care and household products. The invention particularly relates to cosmetic, personal care and household products consisting of oil-in-water emulsions as well as to hydrophobic cosmetic, personal care and household product ingredients containing such monoalkyl citrates.

Various citric acid esters have been known for different uses in cosmetic preparations.

Thus, in EP 006234, EP 006232, and U.S. Pat. No. 4,010,253 the use of citric acid esters of 1–6C alcohols as deodorants in various cosmetic products is decribed. It is stressed that the trialkyl esters are highly preferred for this purpose. It is also stressed that the cosmetic product should have a low water content, preferably below 5% w/w, unless the citric acid ester is used in conjunction with an antioxidant.

In DE 2361716 the use of mixed esters, obtained by complete esterification of citric acid with a mixture of aliphatic diols and 12–30C aliphatic monoalcohols, as water-in-oil emulsifiers is described. The products are suitable for skin creams and the like.

Certain long-chain 2-hydroxyalkylesters of citric acid, obtained by reacting terminal long-chain epoxides with citric acid have been found to be water-in-oil emulsifiers (P. Lorenz et al, 10th IFSCC Congress, Cosmetic Horizons, Sydney, Australia, 25–27th October 1978, Vol 2.).

In EP 199131 derivatives, such as alkali or alkaline earth metal salts, of mono-, di-, or tri-esters of citric acid and polyoxy(2–4C)alkylated mono-(8–20C)-alcohols have been described as emulsifiers which are useful for e.g. cosmetics.

GB 1,448,792 describes mono- and di-esters prepared from citric acid and 12–22C alkyl lactates and their use as emulsifiers in e.g. cosmetics.

In EP 282289 skin-smoothening compositions are disclosed containing salts of monoesters of citric acid and 10–18C alcohols and (poly)ethoxylated alcohols.

Monoesters of citric acid are also employed in the food technology art. U.S. Pat. No. 2,518,678 (Gooding et al.) describes agents said to retard the development of rancidity and improve moisture retention in glyceridic oil compositions, e.g., margarine. These agents, defined at col. 1, line 45 to col. 2, line 25, include monolauryl citrate and monostearyl citrate. Related U.S. Pat. No. 2,523,792 (Vahlteich et al.) describes edible compositions which are said to retard rancidity in glyceridic oils and which have 15 to 37.5% of selected monoesters of citric acid (including monolauryl, monomyristyl, monopalmityl, monooleyl and monostearyl citrate) dissolved in a solubilizing agent, e.g. lecithin. Monoesters of citric acid are also said to retard deterioration of milk and egg products in U.S. Pat. No. 2,667,419 (Gooding et al.). Citric acid monoesters of decanols, dodecanols, hexadecanols, and octadecanols are particularly disclosed and more particularly monolauryl and monostearyl citrate. Also, U.S. Pat. No. 2,902,372 (Harris) discloses monoesters of citric acid with aliphatic alcohols of less than 3 carbon atoms for the purpose of improving the whipping properties of egg whites. Finally, U.S. Pat. No. 3,004,853 (Julian et al.) discloses citric acid esterified with cetyl alcohol as part of an emulsifier system in a liquid shortening.

In the perfumery, cosmetics, personal care and household products industry there is a need for solubilizers which can be used to prepare clear oil-in-water microemulsions of perfumes or other hydrophobic ingredients, which solubilizers are inoccuous to the skin.

It has now been found that mono-alkyl citrates wherein the alkyl group has 7–10 carbon atoms are excellent solubilizers which may be used to provide stable oil-in-water emulsions of perfumes and other hydrophobic liquid ingredients of cosmetic, personal care and household products. They are especially suitable to provide clear o/w microemulsions. To distinguish clear o/w microemulsions from o/w emulsions in general the former will hereinafter be referred to as "microemulsions". Perfumes and other hydrophobic liquid ingredients of cosmetic, personal care and household products will hereinafter be referred to simply as "hydrophobic liquids".

The monoalkyl citrates are completely inoccuous, even to delicate skins. Contrary to what might have been derived from the prior art, they are stable in aqueous media also in the absence of antioxidants. Finally they are completely miscible with most perfume components and other hydrophobic liquids and can therefore be used as diluents for perfumes and other hydrophobic liquids, especially if these are intended to be used in emulsion, particularly in microemulsions.

The invention therefore provides cosmetic, personal care and household products consisting of emulsions comprising an aqueous phase, at least one hydrophobic liquid and a 7–10C monoalkyl citrate. Furthermore, the invention provides mixtures of one or more hydrophobic liquids and 7–10C monoalkyl citrates.

The presence of already relatively small quantities of monoalkyl citrates in hydrophobic liquids gives rise to a clearly noticeable improvement of emulsion stability and ease of emulsification when such ingredients are incorporated in an emulsion type cosmetic or personal care or household product. For microemulsions an improvement of clarity is obtained. Thus, mixtures of hydrophobic liquids and a monoalkyl citrate usefully contain 0.5% w/w or more of the monoalkyl citrate, preferably at least 2% w/w and more preferably at least 5% w/w. On the other hand, such mixtures may comprise up to 95% w/w, preferably up to 90% w/w of the monoalkyl citrate. The monoalkyl citrates are especially useful for solubilizing perfumes and therefore the hydrophobic liquids part in the mixtures mentioned above may consist for a large part (e.g. 50% w/w or more) or even completely of perfume. Other hydrophobic liquids which may be solubilized by the monoalkyl citrates, and therefore be present in relatively large quantities in the hydrophobic liquid mixture, are skin emollients such as isopropyl myristate.

The quantity of monoalkyl citrate to be incorporated in a cosmetic, personal care or household product according to the invention depends on the quantity of hydrophobic liquid to be emulsified and for microemulsions on the desired degree of clarity. Generally the emulsions/microemulsions should contain at least 0.01% w/w, preferably at least 0.1%, more preferably at least 1% w/w of the monoalkyl citrate, whereas a quantity of more than 30% w/w will usually not be required. The preferred monoalkyl citrate for the purposes of the invention is monooctyl citrate.

For the purposes of this invention "cosmetic products" are products intended for increasing the appeal, visually or olfactively, of the human body. Likewise "personal care products" are products intended for cleaning, smoothening or otherwise improve the health and well-being of the outside of the human body. These definitions of cosmetic and personal care products at least partially overlap since many products provide functions in both categories. Examples of such products in microemulsion form are: perfumes and like products known as "eau de toilette" and "eau de parfum", hand and body lotions, skin tonics, shaving products, bath and shower products, deodorant and antiperspirant products, hair care products such as shampoos and hair conditioners, mouth and dental care products. Such products are well known in the art. Thus, examples of skin care products are described in "Harry's Cosmeticology", R. G. Harry, 6th edition, Leonard Hill Books (1973), Chapters 5–13, 18 and 35; examples of deodorants and antiperspirants are described in C. Fox, Cosmetics and Toiletries 100 (December 1985), pp 27–41; examples of hair care products are described in "Harry's Cosmeticology", vide supra, chapters 25–27; examples of dental care products are described in M. Pader, Oral Hygiene: Products and Practice, Marcel Dekker, New York (1988). Cosmetic and personal care products are usually perfumed, on the one hand to to give a pleasant odour to the products themselves and on the other hand to have de body parts to which they are applied emit a pleasant odour after their use.

For the purposes of this invention "household products" are products intended for: laundry and textiles care such as washing, bleaching, softening and ironing; cleaning, disinfecting, scouring, polishing or shining hard surfaces, air treatment such as room deodorizing and air freshening.

The emulsions generally also contain various components which are usually present in cosmetic, personal care or household products and which comprise, depending on the type of product, one or more of: various detergents or emulsifiers of the anionic, cationic, amphoteric or nonionic type; bleaches; scouring powders; various organic solvents such as ethanol or isopropanol; humectants; viscosity modifiers; gelling agents; mineral or vegetable oils; waxes; colourants; pearlescent agents; preservatives; physiological coolants; etc.

The monoalkyl citrates according to the invention have been found to possess antimicrobial properties against various microorganisms which could cause microbiological spoilage in cosmetic, personal care and household products and thus the incorporation of a separate preservative may not be necessary in many cases, or the amount of preservative could be substantially lower than would be necessary without the presence of the monoalkyl citrate.

The monoalkyl citrates may be prepared according to various methods known in the art, e.g. as described in EP 282289.

As used herein, the term "perfume" denotes a substantially water-insoluble composition of matter consisting of one or more perfume components, optionally mixed with a suitable solvent or diluent, which is used to impart a desired odour to the cosmetic, personal care or household product to which it is added and/or to the skin or hair to which this product is applied. Perfume components are those constituents of a perfume which are added thereto only or primarily for their olfactive contribution. Perfume components may be natural such as essential oils, absolutes, resinoids, resins, concretes, etc., and synthetic such as hydrocarbons, alcohols, aldehydes, ketones, ethers, acids, esters, acetals, ketals, nitriles, etc., including saturated and unsaturated compounds, aliphatic, carbocyclic and heterocyclic compounds.

The term "clear" as herein applied to microemulsions denotes a product which is transparant or translucent when observed through a layer of not more than 10 cm thickness. Preferably the cosmetic and personal care products according to the invention have a turbidity of below 45 FTU, more preferably below 35 FTU. Turbidity is measured using a standard turbidity photometer and expressed in American Standard Farmaze Turbidity Units (FTU). The higher the value, the more turbid the solution.

The following examples are intended to illustrate the invention, However, the invention is not limited thereto.

EXAMPLE 1

Two samples of the same perfume were made, one contained 10% w/w of the standard diluent diethyl phthalate whilst the other contained 10% w/w monooctyl citrate instead. Each perfume was added to a standard shampoo base and the turbidity measured using a turbidity photometer. The results are presented below.

|  | % w/w | % w/w |
| --- | --- | --- |
| Shampoo base | 99.7 | 99.7 |
| Perfume with monooctyl citrate | 0.3 | — |
| Perfume with diethyl phthalate | — | 0.3 |
| Total | 100.0 | 100.0 |
| Turbidity (in FTU) | 24.0 | 42.0 |

EXAMPLE 2

Two samples of the same low alcohol aftershave were made according to the recipes below, wherein one contained 3% w/w of monooctyl citrate whereas the other contained 3% w/w extra water. The turbidity of the aftershave was measured using a turbidity photometer. The results are presented below.

|  | % w/w | % w/w |
| --- | --- | --- |
| Perfume | 0.4 | 0.4 |
| Ethanol | 20.0 | 20.0 |
| Water | 76.3 | 79.3 |
| Tris-aminomethane | 0.3 | 0.3 |
| Monooctyl citrate | 3.0 | — |
| Total | 100.0 | 100.0 |
| Turbidity | 27.0 | 163.0 |

EXAMPLE 3

Two samples of the same toner were made according to the recipes below, wherein one contained 3% w/w of monooctyl citrate whereas the other contained 3% w/w extra water. The turbidity of the toner was measured using a turbidity photometer. The results are presented below.

|  | % w/w | % w/w |
| --- | --- | --- |
| Perfume | 0.40 | 0.40 |
| Water | 90.83 | 93.83 |
| Propylene glycol | 5.00 | 5.00 |
| Tris-aminomethane | 0.75 | 0.75 |
| Red 33 (as 0.5% solution) | 0.02 | 0.02 |
| Monooctyl citrate | 3.00 | — |
| Total | 100.00 | 100.00 |
| Turbidity | 3.4 | 558.0 |

EXAMPLE 4

Two samples of the same face mask were made according to the recipes below, wherein one contained 3% w/w of monooctyl citrate whereas the other contained 3% w/w extra water. The turbidity of the face mask was measured using a turbidity photometer. The results are presented below.

|  | % w/w | % w/w |
|---|---|---|
| Perfume | 0.5 | 0.5 |
| Polyvinylpyrrolidon | 5.0 | 5.0 |
| Polyvinyl alcohol (10% aqueous soln.) | 91.0 | 91.0 |
| Water | — | 3.0 |
| Tris-aminomethane | 0.5 | 0.5 |
| Monooctyl citrate | 3.0 | — |
| Total | 100.0 | 100.0 |
| Turbidity | 32.0 | 516.0 |

We claim:

1. Cosmetic, personal care and household products consisting of clear o/w microemulsions comprising an aqueous phase, a hydrophobic liquid and, as a solubilizer for said hydrophobic liquid, a monoalkyl citrate having an alkyl group of 7–10 carbon atoms, said citrate being present in an amount sufficient to stabilize said clear microemulsion.

2. Cosmetic, personal care and household products according to claim 1 wherein the quantity of monoalkyl citrate is 0.01–30% by weight based on the weight of the total emulsion.

3. Cosmetic, personal care and household products according to claim 2 wherein the hydrophobic liquid comprises at least 50% by weight of perfume based on the total weight of the hydrophobic liquid.

4. Cosmetic, personal care and household products according to claim 3 wherein the microemulsion has a turbidity below 45 FTU.

5. Cosmetic, personal care and household products according to claim 4 wherein the monoalkyl citrate is monooctyl citrate.

6. A mixture consisting of one or more hydrophobic liquids and a monoalkyl citrate having an alkyl group of 7–10 carbon atoms.

7. A mixture according to claim 6 wherein the quantity of monoalkyl citrate is 0.5–95% by weight of the mixture.

8. (Amended) A mixture according to claim 7 wherein the hydrophobic liquid comprises at least 50% by weight of perfume based on the total weight of the hydrophobic liquid.

9. A mixture according to claim 6 wherein the monoalkyl citrate is monooctyl citrate.

* * * * *